United States Patent [19]

Ellendt et al.

[11] 4,189,354
[45] Feb. 19, 1980

[54] PROCESS FOR THE PRODUCTION OF DIISOCYANATODIPHENYL METHANE ISOMERS WITH AN ADJUSTED CONTENT OF CHLORINE COMPOUNDS

[75] Inventors: Günther Ellendt, Krefeld; Hermann Fischer, Leverkusen; Peter Fischer, Krefeld, all of Fed. Rep. of Germany

[73] Assignee: Bayer Aktiengesellschaft, Leverkusen, Fed. Rep. of Germany

[21] Appl. No.: 908,319

[22] Filed: May 22, 1978

Related U.S. Application Data

[63] Continuation-in-part of Ser. No. 811,819, Jun. 30, 1977, abandoned.

[30] Foreign Application Priority Data

Jul. 10, 1976 [DE] Fed. Rep. of Germany ....... 2631168

[51] Int. Cl.$^2$ .................... B01D 3/10; C07C 119/04
[52] U.S. Cl. ................................. 203/81; 203/77; 203/82; 260/453 SP
[58] Field of Search ................................. 203/81–85, 203/71, 73–79; 260/453 SP

[56] References Cited

U.S. PATENT DOCUMENTS

| | | | |
|---|---|---|---|
| 3,658,656 | 4/1972 | Adica et al. | 260/453 SP |
| 3,857,871 | 12/1974 | Hatfield et al. | 260/453 SP |
| 3,897,314 | 7/1975 | Liebsch et al. | 260/453 SP |
| 3,912,600 | 10/1975 | Hatfield et al. | 260/453 SP |

FOREIGN PATENT DOCUMENTS

| | | | |
|---|---|---|---|
| 49-13786 | 4/1974 | Japan | 260/453 SP |
| 397512 | 1/1974 | U.S.S.R. | 260/453 SP |

*Primary Examiner*—Wilbur L. Bascomb, Jr.
*Attorney, Agent, or Firm*—Gene Harsh; Joseph C. Gil; R. Brent Olson

[57] ABSTRACT

The instant invention is directed to a process for the production of diisocyanatodiphenyl methane isomers having an adjusted content of chlorine compounds comprising:
(a) separating diisocyanatodiphenyl methane isomers from a polyisocyanate mixture of the diphenyl methane series in a first distillation stage,
(b) subjecting said separated isomers to a second distillation stage using a recycle ratio of from 0.1 to 10 and wherein from 0.5 to 10% by weight of the feed into said second distillation stage is run off as the sump product,
(c) subjecting the head product of said second distillation stage to a third distillation stage whereby readily volatile impurities are freed therefrom, and
(d) working up the sump product of said third distillation stage to obtain purified 4,4'-diisocyanatodiphenyl methane and, optionally, purified 2,4'-diisocyanatodiphenyl methane.

6 Claims, 4 Drawing Figures

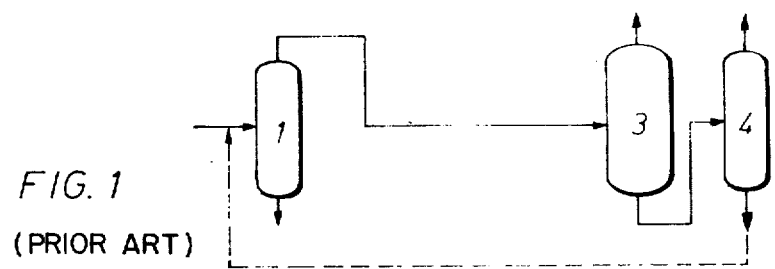
FIG. 1
(PRIOR ART)
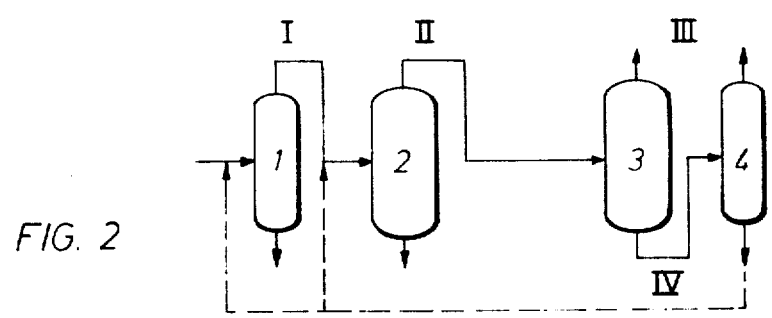
FIG. 2
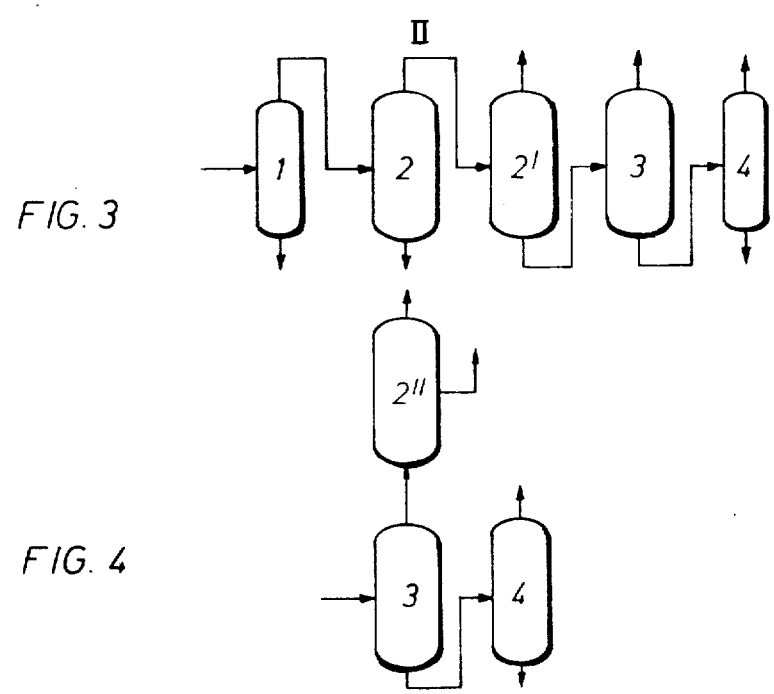
FIG. 3
FIG. 4

PROCESS FOR THE PRODUCTION OF DIISOCYANATODIPHENYL METHANE ISOMERS WITH AN ADJUSTED CONTENT OF CHLORINE COMPOUNDS

This application is a continuation-in-part of our co-pending application Ser. No. 811,819 filed June 30, 1977, now abandoned.

BACKGROUND OF THE INVENTION 2,4'-diisocyanatodiphenyl methane and, in particular, 4,4'-diisocyanatodiphenyl methane are important starting materials for the production of polyurethane plastics.

In the condensation of aniline and formaldehyde in the presence of acid catalysts, followed by reaction of the polyamine mixtures formed with phosgene, the isomeric compounds 2,2'-, 2,4'- and 4,4'-diisocyanatodiphenyl methane are simultaneously formed. These isomers have been found to contain varying amounts of impurities, including those which contain organically-bound chlorine in the form of hydrolyzable chlorine. Compounds containing hydrolyzable chlorine can adversely affect the reaction of isocyanates with polyols to form polyurethanes because these chlorine compounds influence the velocity of the reaction and in general, retard it. Accordingly, the hydrolyzable chlorine content of isocyanates is an important parameter when considering the purity thereof. Compounds containing hydrolyzable chlorine include, for example, the reaction products of phosgene with secondary products from the condensation of aniline and formaldehyde, such as p-aminobenzyl aniline, N-methylamino compounds, acridane and acridine (acridine being obtainable from acridane by a redox reaction).

It is known that impurities may be removed from distillable isocyanates by processes which are either based on the addition of compounds capable of converting chlorine-containing impurities into a less volatile form such as (see, e.g. German Pat. No. 1,138,040) or by a technically complex physical separation process (such as crystallization as described in German Offenlegungsschrift No. 1,938,384). As commercial products, diisocyanatodiphenyl methanes, obtained by fractional distillation from a polyisocyanate mixture, are mixtures of isomers. The ratio of the various isomers is governed by the composition of the polyamine mixture used and by the effort involved in the fractionation of the isocyanates.

Because of the low concentration thereof, the multiplicity thereof and to a certain extent, the sensitivity thereof to heat and changes caused by inter-reaction, the chlorine-containing compounds present in the commercially produced diisocyanates are difficult to analyze. The literature describes splitting reactions of N,N-disubstituted carbamic acid chlorides which, depending on the substituents and the presence of catalysts, may take place at temperatures above 150° C., at which temperature, diphenyl methane diisocyanates are generally distilled. Such splitting reactions, in which substantially involatile chlorine-containing compounds are converted into lower boiling compounds [such as conversion of the acid chloride formed from phosgene and p-aminobenzyl aniline into p-isocyanatobenzyl chloride and phenyl isocyanate (J. Org. Chem. 39 (1974), 2897–2899)], also alter the chlorine function. Thus, a readily hydrolyzable chlorine in a carbamic acid chloride becomes a more firmly bound chlorine in a benzyl chloride function.

In conventional distillation-based purification processes (German Auslegeschrift No. 1,923,214), separation of the solvents used for the amine/phosgene reaction is generally followed by purification in the following stages: Removal of diisocyanate from a polyisocyanate mixture by distillation, separation of the isomeric diphenyl methane diisocyanates by fractional distillation in a column and distilling off diisocyanate of reduced 2,4'-diisocyanatodiphenyl methane content from polymerization products which are reformed during distillation by the action of heat on isocyanates. The chlorine-containing impurities are only unsatisfactorily separated off by this process, probably because reactions of the type described above continuously take place during the thermal stressing of the distillation process.

BRIEF DESCRIPTION OF THE DRAWINGS

FIG. 1 schematically represents the prior art process.
FIGS. 2, 3 and 4 schematically represent various embodiments of the instant invention.

DESCRIPTION OF THE INVENTION

It has now surprisingly been found that these difficulties may be obviated and that highly pure diisocyanates, which may be exactly adjusted in regard to their chlorine content, may be obtained by initially freeing the isomer mixture obtained by distillation based separation of a polyisocyanate mixture of the diphenyl methane series obtained by the phosgenation of aniline/formaldehyde condensates and consisting essentially of 2,4'- and 4,4'-diisocyanatodiphenyl methane, apart from small quantities of 2,2'-diisocyanatodiphenyl methane, from most of the impurities boiling at temperatures higher than 4,4'-diisocyanatodiphenyl methane in a distillation column (2) using a recycle ratio (the ratio by volume of recycle to distillate removed) of from 0.1 to 10 and subsequently freeing the thus obtained distillate from the impurities boiling at temperatures lower than 2,4'-diisocyanatodiphenyl methane. The total amount of vapor which reaches the top of a distillation column is referred to as the load. In a recycle column, a part of the load, vapor reaching the top of the column, is condensed and the condensed vapors are recycled. The remaining vapors are removed as distillate with or without being condensed.

Accordingly, the present invention relates to a process for the production of diisocyanatodiphenyl methane isomers with an adjusted content of chlorine compounds by the distillation-based separation of diisocyanatodiphenyl methane isomers from a polyisocyanate mixture of the diphenyl methane series obtained by the phosgenation of aniline/formaldehyde condensates in a distillation stage (1) and further distillation-based purification of the resulting fraction (I), distinguished by the fact that the fraction (I) is distilled in a distillation column (FIGS. 2 and 3, number 2) using a recycle ratio of from 0.1 to 10. From 0.5 to 10%, by weight, of the total amount of fraction (I) introduced into the column (2) is run off as the sump product of the column, after which the fraction (II) obtained as the head product of the column is freed in the following distillation stage from readily volatile impurities and, optionally, from 2,4'-diisocyanatodiphenyl methane as well. Finally, the sump product obtained is worked-up in known manner into purified 4,4'-diisocyanatodiphenyl methane and optionally purified 2,4'-diisocyanatodiphenyl methane.

The most important embodiments of the process according to the present invention are described in more detail below with reference to the accompanying drawings.

FIG. 1 shows the conventional process. The number (1) denotes the distillation stage in which the diisocyanatodiphenyl methane isomers are separated from the polyisocyanate mixture of the diphenyl methane series. In a distillation column (3), the isomers are then separated into a head product, which contains most of the 2,2'- and 2,4'-isomers, and a sump product from which pure 4,4'-diisocyanatodiphenyl methane (head product) and polymers formed during distillation (sump) are obtained in a third distillation column (4).

FIG. 2 shows an embodiment of the process according to the present invention, in which an isomer mixture obtained as fraction (I) by distillation from a polyisocyanate mixture of the diphenyl methane series (distillation stage (1)) and consisting essentially of 2,4'- and 4,4'-isomers, and small quantities of 2,2'-diisocyanatodiphenyl methane, is split in a distillation column (2) into a fraction (II) (head product) and a sump, most of the impurities boiling at temperatures higher than 4,4'-diisocyanatodiphenyl methane remaining in the sump (2), while the impurities boiling at temperatures lower than 4,4'-diisocyanatodiphenyl methane which are already present in fraction (I) and which are formed thermally in (2) are delivered together with fraction (II) into a distillation column (3) where separation into a fraction (III) and a sump (IV) takes place. The fraction (III) obtained contains most of the 2,2'- and 2,4'-isomers in addition to the impurities boiling at temperatures lower than 4,4'-diisocyanatodiphenyl methane. Finally, the sump (IV) is split in a last column (4) into pure 4,4'-diisocyanatodiphenyl methane (V) (head product) and a residue (VI) (sump).

FIG. 3 shows another embodiment of the process according to the present invention, in which the fraction (II) obtained from column (2) is first separated by distillation in another column (2') in such a way that most of the impurities boiling at temperatures lower than 2,4'-diisocyanatodiphenyl methane are separated off as head product, while most of the 2,4'- and 4,4'-diisocyanatodiphenyl methane remains in the sump. This sump is finally separated in columns (3) and (4) into 2,4'-diisocyanatodiphenyl methane having a depleted content of chlorine-containing impurities (head product of column (3)), 4,4'-diisocyanatodiphenyl methane having a depleted content of chlorine-containing impurities (head product of column (4)) and residue (sump product of column (4)).

Finally, FIG. 4 shows another embodiment of the process according to the present invention relating to a division of the fraction (II) emanating from column (2). In this embodiment, a column (2") is arranged at the head of the column (3), which enables the chlorine compounds boiling at temperatures lower than 2,4'-diisocyanatodiphenyl methane together with small quantities of 2,2'-diisocyanatodiphenyl methane to be separated off at the head of the column (2"), while 2,4'-diisocyanatodiphenyl methane largely freed from chlorine-containing impurities is obtained as a side stream of the column (2"). The column (4) enables the sump from column (3) to be separated into 4,4'-diisocyanatodiphenyl methane substantially free of chlorine-containing impurities and a distillation residue.

The process according to the present invention is not just a simple distillation-based separation of the chlorine-containing impurities. On the contrary, partial conversion of the substantially involatile impurities originally present into readily volatile impurities is obtained in column (2). The thus-obtained readily volatile impurities are subsequently removed in columns (2'), (2") and/or (3). The separation effect obtained in the process according to the present invention is quite clearly also attributable to this separate conversion of substantially involatile chlorine compounds into readily volatile chlorine compounds. The distillation column (3) used in the above-described conventional process was obviously ineffective for this purpose because the conversion cannot be carried out simultaneously with a clean separation of the end products and impurities in a single column.

In all the embodiments of the process according to the present invention, high-boiling impurities are removed from the diisocyanate mixture (fraction (I)) in a distillation step by fractionation in a column (2) to such an extent that the end-products obtained have a substantially reduced, adjusted content of hydrolyzable chlorine. This chlorine content may be brought after or in combination with the separation of the isomers to a content of less than 50 ppm of total chlorine and 10 ppm of hydrolyzable chlorine. It is important to separate off impurities boiling at temperatures higher than 4,4'-diisocyanatodiphenyl methane or to convert them at least partly into lower boiling impurities in column (2), because these substantially involatile impurities generally contain most of the hydrolyzable chlorine in the distillate from the separation of the diisocyanate/polyisocyanate mixture. Some of the compounds containing hydrolyzable chlorine boil at temperatures lower than 2,4'-diisocyanatodiphenyl methane. Since the high-boiling chlorine compounds are separated off and since low-boiling chlorine compounds cannot be continually reformed by rearrangements and other secondary reactions, the separation of these secondary products in the columns (2'), (2") and (3) is possible with considerably more effect and to a far greater extent than in the conventional process. Accordingly, in order to adjust the content of hydrolyzable chlorine, it is now sufficient to run off sump product containing chlorine in a column (2) which precedes the column (3) for the separation of 2,4'- and 4,4'-diisocyanatodiphenyl methane. The result of such a measure must be regarded as surprising since it could not be calculated or predicted from experience because of (a) the relatively high volatility of the compounds which distill over with the diisocyanate during separation of the diisocyanate/polyisocyanate mixture, (b) the tendency thereof to decompose, (c) the possibility of a back reaction of chlorine-containing cleavage products with NCO-groups to form adducts, including the formation of carbamic acid chloride from isocyanate and hydrogen chloride, and, finally, (d) the absence of accurate analytical methods for determination of all the various individual chemical compounds. Despite the inclusion of a column (2) and the resulting additional thermal stressing of the product introduced into stages (3) and (4), the total amount of polymer obtained in the sumps of (2) and (4) is not considerably increased, which is indicative of the fact that substances accelerating the catalytic polymerization during isomer separation are also removed in the sump of column (2).

It is also possible by the process according to the present invention, following separation of the compounds containing hydrolyzable chlorine and boiling at temperatures higher than 4,4'-diisocyanatodiphenyl methane, to run off the compounds containing hydrolyzable chlorine and boiling at temperatures lower than 2,4'-diisocyanatodiphenyl methane as head product by fractionation in another column (2') and in this way to obtain a product enriched with 2,4'-diisocyanatodiphenyl methane and containing less than 50 ppm of total chlorine and less than 10 ppm of hydrolyzable chlorine (FIG. 3). It is also possible to obtain either in the same operation or in an additional operation 2,2'-diisocyanatodiphenyl methane which boils at a temperature lower than 2,4'-diisocyanatodiphenyl methane and whose separation from 2,4'-diisocyanatodiphenyl methane may be carried out in basically the same way as the separation of 2,4'-/4,4'-diisocyanatodiphenyl methane.

In all cases, the separation of diisocyanates from a polyisocyanate mixture in the distillation stage (1) takes place under the most moderate conditions possible in a good vacuum of less than 15 mbars and without fractionation in order not unnecessarily to damage the mixtures of MDI-polymer obtained as secondary yield as the sump of (1). It is known that decomposition reactions take place more quickly in non-purified polyisocyanate mixtures, produced from nondistilled aniline/formaldehyde condensates by reaction with phosgene, than in diphenyl methane diisocyanates which have been obtained by distillation from such polyisocyanate mixtures. A large amount of those compounds which would promote thermal decomposition of the required diisocyanates and the formation of carbodiimides during the subsequent distillation steps is separated off in the distillation stage (1). However, the distillate inevitably also contains small quantities of compounds which boil at temperatures higher than the isomeric diphenyl methane diisocyanates, such as the reaction product of phosgene and hydrogen chloride with p-aminobenzyl aniline, N-methyl amino compounds and acridine.

The higher boiling compounds are removed by fractional distillation (2) in a column with a low pressure loss to such an extent that chlorine compounds only remain in the distillate in the required low concentration. Suitable low pressure loss columns include inter alia, columns having fabric packings or helical springs and the like. Such columns are known in the art and described i.e., by A. Sperandion, M. Richard and M. Huber in "Chemie-Ingenieur-Technik" (1965) or by H. J. Kloss in "Chemiker-Zeitung,"95, (1971), pages 556–562.

These columns may either be fed in the vapor phase from the preceding separation of diisocyanate and higher boiling polyisocyanates, or in the liquid phase after intermediate condensation of the in-flowing diisocyanate. In addition to the distillation section, the column may also have a concentrating section.

These columns are preferably operated under a vacuum of less than 20 mbar. The sump temperature is generally from about 170° to about 240° C., and preferably from about 180° to about 215° C. In the column, (2), from 0.5 to 10%, by weight, of the fraction (I) obtained from the distillation stage (1) is generally run off as sump. The recycle ratio in column (2) is from 0.1 to 10. The head distillate removed from this distillation stage still contains those compounds containing hydrolyzable chlorine which boil at temperatures lower than the isomeric diphenyl methane diisocyanates.

The recovery of 2,4'-diisocyanatodiphenyl methane, optionally in admixture with isomers, takes place by fractional distillation in another low pressure loss column (3) and under similar temperatures and pressures to those prevailing in column (2). In general, the distillation column (3) is also operated using a recycle ratio of from 1 to 10.

Another fractionation column (2') may optionally be arranged between these two columns for separating off 2,2'-diisocyanatodiphenyl methane. By virtue of this arrangement, it is also possible to remove chlorine-containing compounds which boil at temperatures lower than 2,4'-diisocyanatodiphenyl methane and to obtain in the column (3) a head product with enriched 2,4'-diisocyanatodiphenyl methane and a content of less than 50 ppm of total chlorine and less than 10 ppm of hydrolyzable chlorine.

Other possible arrangements include column structures having several distillate outlets, for example at the head for a small quantity of 2,2'-diisocyanatodiphenyl methane and chlorine compounds, and at an underlying plate for a side stream outlet for a product which, by comparison with the head product, contains less 2,2'-diisocyanatodiphenyl methane and chlorine compounds and more 2,4'-diisocyanatodiphenyl methane. This arrangement corresponds to a combination of columns (2) and (3) arranged one above the other with a common evaporator at the sump of column (3) (FIG. 4).

By virtue of the process according to the present invention, it is now possible to produce 2,4'-diisocyanatodiphenyl methane in pure form having a content of more than 97% of the pure isomer and less than 50 ppm of chlorine.

Working-up of the sump product of column (3), which gives 2,4'-diisocyanatodiphenyl methane as head product, is carried out in the conventional way in another following distillation column (4), in which polymer formed during distillation is separated from pure 4,4'-diisocyanatodiphenyl methane, optionally in admixture with isomers.

The sump of the distillation column (4), in which the diisocyanate remains, may, because of the danger of the auto-catalytically accelerated formation of relatively high molecular weight products on enrichment with carbodiimides, be recycled to the distillation stage (1) where it is mixed with the polyisocyanate mixture from the phosgenation stage and separated into diisocyanate as distillate and a sump containing the relatively high boiling components. If the sump product from (4), containing carbodiimide and other basic compounds, is added with the input for column (2), the reactions which take place in (2), such as the splitting of chlorine compound on the one hand and the binding of acid chlorides with basic compounds on the other hand, and hence the controlled separation of chlorine-containing compounds from diphenyl methane diisocyanate may be promoted. In this case, the sump from (4) is removed from the system together with the sump from (2).

Basically, it is possible to produce from the sump products of all the distillation stages mixtures which may be used as valuable starting materials for the production of polyurethane plastics, especially foams.

The extreme purification of 4,4'-diisocyanatodiphenyl methane and 2,4'-diisocyanatodiphenyl methane obtainable by the process according to the present invention is of considerable commercial significance because 4,4'-diisocyanatodiphenyl methane, like 2,4'-diisocyanatodiphenyl methane of low chlorine content, is particularly resistant to yellowing and to the effects of light and air so that, in many cases, there is no need to add stabilizers which prevent discoloration.

Another significant advantage of the process according to the present invention is that it is also possible, for obtaining 2,4'- and 4,4'-diisocyanatodiphenyl methane or mixtures thereof with an adjusted content of chlorine compounds, to use aniline-formaldehyde condensates produced by a variety of different processes and containing a varying amount of compounds containing secondary or tertiary nitrogen, such as p-aminobenzyl aniline, N-methylamino compounds, acridine and acridane. Accordingly, the quality of the end-products is largely independent of the quality of the polyamine and polyisocyanate mixtures used as starting products.

The process according to the present invention is illustrated by the following Examples:

EXAMPLES

EXAMPLE 1

(A) Comparison: conventional process

A polyisocyanate mixture of the diphenyl methane series containing approximately:

2.3% of 2,4'-diisocyanatodiphenyl methane,
  81.9% of 4,4'-diisocyanatodiphenyl methane,
  11.7% of 3-nuclear compounds
  0.9% of 4-nuclear compounds as determined by gas chromatography, is worked-up in a continuously operated distillation unit with the sections (1), (3) and (4) (FIG. 1).

(1), (3) and (4) are apparatus with evaporators, pumps for delivering product, condensers for the distillate and connection to a vacuum system which maintains a pressure of 10 mbar for (1) and a pressure of 5 mbar for (3) and (4), as measured at the product inlet to the condenser.

A column consisting of six 2 meter long drops filled with helical springs (Montz system) is arranged at (3) between the evaporator and condenser.

The product flows in at the fourth drop, counting upwards. The column load, i.e. the total of recycle and distillate removed, is adjusted to 1000 kg/h.

A separation of diisocyanate/polyisocyanate mixture takes place in distillation stage (1). (3) receives distillate from (1) as input, the head product being an isocyanate mixture enriched with 2,4'-diisocyanatodiphenyl methane.

A distillate predominantly containing 4,4'-diisocyanatodiphenyl methane is obtained in (4), the sump running back to the entrance to the distillation stage (1).

950 parts per hour of a distillate containing 400 ppm of hydrolyzable chlorine (=HC) and 1280 ppm of total chlorine (=TC)

are obtained in the distillation stage (1). This distillate from (1) is the starting product for the distillation (3) in which a separation of isomers takes place:

Distillate from (3) 75 kg/h with
  240 ppm of HC
  570 ppm of TC

Purification in the distillation stage (4) produces a distillate (760 kg/h) with
  80 ppm of HC
  280 ppm of TC and
  115 kg/h of sump product which is recycled to (1)

If a polyurethane test specimen is produced from this distillate with 1.0% of 2,4'-diisocyanatodiphenyl methane and 98.9% of 4,4'-diisocyanatodiphenyl methane and heat treated at 200° C., it undergoes discoloration, becoming yellow-brown in color.

(B) Comparison: new process

In the existing distillation unit with the sections (1), (3) and (4), another column (2) which is identical in equipment and size with column (3) is connected between (1) and (3) (FIG. 2). The quality of the starting product and distillate from (1) are the same as in comparison (A), the quantity of distillate from (1) is, however, only 920 kg/h.

A distillate (850 kg/h) with
  160 ppm of HC
  280 ppm of TC is removed at the head of column (2), the load of which is adjusted to be 1300 kg/h which corresponds to a recycle of 450 kg/h, while a sump product (70 kg/h) with
  2200 ppm of HC
  3200 ppm of TC is removed at the foot of this column.

A distillate enriched with 2,4'-diisocyanatodiphenyl methane and containing
  115 ppm of HC
  280 ppm of TC is obtained at a rate of 75 kg/h in the distillation (3).

4,4'-diisocyanatodiphenyl methane containing 1.2% of 2,4'-diisocyanatodiphenyl methane and
  4 ppm of HC
  12 ppm of TC distills from the final stage (4).

A polyurethane test specimen produced and tested in the same way as in test (A) using the distillate of (4) remains almost white after the heat treatment.

EXAMPLE 2

The arrangement of the distillation apparatus is the same as in Example 1 (B). A polyisocyanate mixture of the diphenyl methane series is used, containing approximately:

61.6% of 2-nuclear compounds
  25.1% of 3-nuclear compounds
  10.9% of 4-nuclear compounds
  1.5% of 5-nuclear compounds approximately 3.3% of the 2-nuclear compounds consisting of 2,2'-diisocyanatodiphenyl methane, 25.2% of 2,4'-diisocyanatodiphenyl methane, 70.1% of 4,4'-diisocyanatodiphenyl methane and 1.3% of N-methyl compounds.

The following products were obtained:

| Distillate from kg/h | | Content ppm | | Content % | |
| --- | --- | --- | --- | --- | --- |
| | | HC | TC | 2,2'- | 2,4'- |
| (1) | 400 | 730 | 1350 | 3.5 | 25.3 |
| (2)* | 380 | 240 | 460 | 3.8 | 26.1 |
| (3) | 180 | 190 | 960 | 7.9 | 55.4 |
| (4) | 180 | 20 | 70 | 0.1 | 1.2 |

*recycle in column (2) : 620 kg/h

Part of the distillate from (3) is distilled a second time through the columns (2) and (3), the only difference being that, corresponding to the arrangement (FIG. 3), the sump product from (2') is delivered to the distillation stage (3):
Input to (2') 400 kg/h with
7.9% of 2,2'-diisocyanatodiphenyl methane
55.4% of 2,4'-diisocyanatodiphenyl methane
190 ppm of HC
960 ppm of TC
The load of column (2') is adjusted to be 1300 kg/h at a recycle of 1250 kg/h corresponding to 50 kg/h of distillate consisting of
61.0% of 2,2'-diisocyanatodiphenyl methane
39.0% of 2,4'-diisocyanatodiphenyl methane
Distillate from (3) 180 kg/h with
0.6% of 2,2'-diisocyanatodiphenyl methane
97.7% of 2,4'-diisocyanatodiphenyl methane
8 ppm of HC
30 ppm of GC

EXAMPLE 3

A polyisocyanate mixture is produced by phosgenation of a polyamine mixture, obtained by aniline/formaldehyde condensation, containing approximately 60% of 2-nuclear compounds, of which 0.5% consist of acridane, 5.9% of 2,2'-diaminodiphenyl methane, 46.6% of 2,4'-diaminodiphenyl methane, 46.6% of 4,4'-diaminodiphenyl methane and 0.5% of N-methyl-substituted diamine, and processed in the same way as described in Example 1B.
Distillate from (1) 400 kg/h with
6.1% of 2,2'-diisocyanatodiphenyl methane
46.9% of 2,4'-diisocyanatodiphenyl methane
550 ppm of HC is delivered together with 30 kg/h of sump product from column (4) to column (2) which is run at a load of 1000 kg/h corresponding to a quantity of recycle of 580 kg/h and a quantity of distillate of 420 kg/h with
5.8% of 2,2'-diisocyanatodiphenyl methane
44.7% of 2,4'-diisocyanatodiphenyl methane
49.5% of 4,4'-diisocyanatodiphenyl methane
The sump product of (2) consisting of 10 kg/h of chlorine containing high boiling compounds. The distillate from (2) is delivered to (3).
Distillate from (3) 240 kg/h with
9.7% of 2,2'-diisocyanatodiphenyl methane
74.2% of 2,4'-diisocyanatodiphenyl methane
150 ppm of HC
Distillate from (4) 150 kg/h with
0.2% of 2,2'-diisocyanatodiphenyl methane
2.2% of 2,4'-diisocyanatodiphenyl methane
97.6% of 4,4'-diisocyanatodiphenyl methane
10 ppm of HC

EXAMPLE 4

A polyisocyanate mixture of the diphenyl methane series with a viscosity of 70 mPas/25° C.
0.2% of 2,2'-diisocyanatodiphenyl methane
4.8% of 2,4'-diisocyanatodiphenyl methane
65.9% of 4,4'-diisocyanatodiphenyl methane
0.3% of N-methyl compounds
21.0% of 3-nuclear compounds
1300 ppm of HC
2700 ppm of TC
is processed by distillation in the same way as described in the Example 1B.
Input to (1) 1200 kg/h;
Distillate from (1) 480 kg/h with
0.3% of 2,2'-diisocyanatodiphenyl methane
6.1% of 2,4'-diisocyanatodiphenyl methane
93.5% of 4,4'-diisocyanatodiphenyl methane
0.1% of N-methyl compounds
360 ppm of HC
570 ppm of TC
Sump from (1) 720 kg/h having a viscosity of 290 mPas/25° C.
3.9% of 2,4'-diisocyanatodiphenyl methane
48.8% of 4,4'-diisocyanatodiphenyl methane
0.4% of N-methyl compounds
34.0% of 3-nuclear compounds
1400 ppm of HC
3900 ppm of TC
Distillate from (2) 520 kg/h (load 1000 kg/h, recycle 480 kg/h) Sump from (2) 30 kg/h with
1650 ppm of HC
2840 ppm of TC
Distillate from (3) 30 kg/h with
4.8% of 2,2'-diisocyanatodiphenyl methane
61.7% of 2,4'-diisocyanatodiphenyl methane
33.5% of 4,4'-diisocyanatodiphenyl methane
Distillate from (4) 420 kg/h with
1.9% of 2,4'-diisocyanatodiphenyl methane
98.0% of 4,4'-diisocyanatodiphenyl methane
4 ppm of HC
12 ppm of TC
Color (Hazen scale) after storage for 10 days under nitrogen at 40° C.:
APHA 5. The method applied is described in "Standard Methods for the Examination of Water Sewage and Industrial Wastes," 9th edition 1947.
The sump from (4) (70 kg/h) goes back into column (2) together with distillate from (1).
4,4'-diisocyanatodiphenyl methane from comparable starting product, produced without the processing stage (2), contains
55 ppm of HC
135 ppm of TC
and after 10 days gives color values of APHA 70.

What is claimed is:
1. A process for the production of diisocyanatodiphenyl methane isomers having an adjusted content of chlorine compounds comprising the steps of:
   (a) subjecting a polyisocyanate mixture of the diphenyl methane series to a first distillation stage whereby diisocyanatodiphenyl methane isomers are obtained as head product;
   (b) subjecting said head product to a second distillation stage using a recycle ratio of from 0.1 to 10 and wherein from 0.5 to 10% by weight of the feed into said second distillation stage is removed as the sump product;
   (c) subjecting the head product of said second distillation stage to a third distillation stage whereby readily volatile impurities are freed therefrom; and
   (d) working up the sump product of said third distillation stage to obtain purified 2,4'- and 4,4'-diisocyanatodiphenyl methane.
2. The process of claim 1, wherein said step (c) comprises:
   (c1) subjecting the head product of said second distillation stage to an intermediate distillation stage using a recycle ratio of from 0.1 to 10, whereby readily volatile impurities are removed therefrom, and
   (c2) subjecting the sump obtained in said intermediate distillation stage, said sump containing most of the 2,4'- and 4,4'-isomers, to said third distillation stage, whereby purified 2,4'-diisocyanatodiphenyl methane is obtained as head product.

3. The process of claim 1, wherein the sump product of said step (d) is worked up to obtain purified 4,4'-diisocyanatodiphenyl methane.

4. A process for the production of diisocyanatodiphenyl methane isomers having an adjusted content of chlorine compounds comprising the steps of:
   (a) subjecting a polyisocyanate mixture of the diphenyl methane series to a first distillation stage whereby diisocyanatodiphenyl methane isomers are obtained as head product;
   (b) subjecting said head product to a second distillation stage using a recycle ratio of from 0.1 to 10 and wherein from 0.5 to 10% by weight of the feed into said second distillation stage is removed as the sump product;
   (c) subjecting the head product of said second distillation stage to a third distillation stage whereby readily volatile impurities and 2,4'-diisocyanatodiphenyl methane are freed therefrom; and
   (d) working up the sump product of said third distillation stage to obtain purified 4,4'-diisocyanatodiphenyl methane.

5. A process for the production of diisocyanatodiphenyl methane isomers having an adjusted content of chlorine compounds comprising the steps of:
   (a) subjecting a polyisocyanate mixture of the diphenyl methane series to a first distillation stage whereby diisocyanatodiphenyl methane isomers are obtained as head product;
   (b) subjecting said head product to a second distillation stage using a recycle ratio of from 0.1 to 10 and wherein from 0.5 to 10% by weight of the feed into said second distillation stage is removed as the sump product;
   (c) subjecting the head product of said second distillation stage to a third distillation stage whereby most of the 2,4'-diisocyanatodiphenyl methane and most of the impurities boiling at temperatures lower than 4,4'-diisocyanatodiphenyl methane are freed therefrom and wherein the recycle ratio of said third distillation stage is from 0.1 to 10; and
   (d) working up the sump product of said third distillation stage to obtain the remaining 2,4'-diisocyanatodiphenyl methane and purified 4,4'-diisocyanatodiphenyl methane.

6. The process of claim 5, wherein the head product of step (c) is subjected to a distillation stage to thereby separate the readily volatile impurities from the 2,4'-diisocyanatodiphenyl methane.

* * * * *